(12) United States Patent
Blomquist et al.

(10) Patent No.: US 8,863,742 B2
(45) Date of Patent: Oct. 21, 2014

(54) CONTROL UNIT AND DISPLAY UNIT FOR AN EMG CONTROLLED VENTILATOR

(75) Inventors: Karin Blomquist, Sollentuna (SE); Fredrik Jalde, Bromma (SE)

(73) Assignee: Maquet Critical Care AB, Solna (SE)

( * ) Notice: Subject to any disclaimer, the term of this patent is extended or adjusted under 35 U.S.C. 154(b) by 560 days.

(21) Appl. No.: 12/597,642

(22) PCT Filed: Apr. 27, 2007

(86) PCT No.: PCT/EP2007/054149
§ 371 (c)(1),
(2), (4) Date: Apr. 9, 2010

(87) PCT Pub. No.: WO2008/131797
PCT Pub. Date: Nov. 6, 2008

(65) Prior Publication Data
US 2010/0180896 A1    Jul. 22, 2010

(51) Int. Cl.
| | | |
|---|---|---|
| *A61M 16/00* | (2006.01) | |
| *A61B 5/06* | (2006.01) | |
| *A61B 5/0488* | (2006.01) | |
| *A62B 7/00* | (2006.01) | |
| *F16K 31/02* | (2006.01) | |
| *A61M 16/12* | (2006.01) | |

(52) U.S. Cl.
CPC ...... *A61B 5/04884* (2013.01); *A61M 2205/584* (2013.01); *A61M 2205/3331* (2013.01); *A61M 16/12* (2013.01); *A61M 16/0051* (2013.01); *A61M 2210/105* (2013.01); *A61M 2230/60* (2013.01); *A61M 2205/502* (2013.01); *A61B 5/06* (2013.01); *A61M 2210/1014* (2013.01); *A61M 2230/08* (2013.01)
USPC .................................................. 128/204.23

(58) Field of Classification Search
CPC ..................... A61M 16/00; A61M 2016/0021; A61M 2016/0069; A61M 16/0051; A61M 16/12; A61M 2016/127; A61M 16/0075; B63C 11/24

USPC .......... 600/546, 554; 128/204.23, 204.18, 23, 128/21, 22, 25, 24, 28, 207.12, 204.21, 128/204.22, 204.25, 204.24, 204.28; 715/275

See application file for complete search history.

(56) References Cited

U.S. PATENT DOCUMENTS

| | | | |
|---|---|---|---|
| 5,520,192 A | 5/1996 | Kitney et al. | |
| 5,671,752 A * | 9/1997 | Sinderby et al. | ............... 600/546 |
| 5,820,560 A * | 10/1998 | Sinderby et al. | ............... 600/546 |
| 6,588,423 B1 | 7/2003 | Sinderby | |
| 6,962,155 B1 * | 11/2005 | Sinderby | ................... 128/204.23 |
| 7,784,461 B2 * | 8/2010 | Figueiredo et al. | ...... 128/204.23 |
| 8,052,621 B2 * | 11/2011 | Wallace et al. | ............... 600/587 |
| 2003/0226565 A1 | 12/2003 | Sinderby et al. | |
| 2005/0096527 A1 * | 5/2005 | Zeller et al. | .................... 600/407 |

FOREIGN PATENT DOCUMENTS

| | | |
|---|---|---|
| WO | WO 98/48877 | 11/1998 |
| WO | WO 99/44374 | 9/1999 |
| WO | WO 99/62580 | 12/1999 |
| WO | WO 2005/048838 | 6/2005 |
| WO | WO 2006/131149 | 12/2006 |

* cited by examiner

*Primary Examiner* — Tan-Uyen T Ho
*Assistant Examiner* — Mark Wardas
(74) *Attorney, Agent, or Firm* — Schiff Hardin LLP

(57) ABSTRACT

A control unit for controlling a ventilator that provides EMG controlled ventilation to a patient receives EMG signals from an esophageal catheter inserted into the patient and selects, dependent on the EMG signal, at least one signal for controlling the ventilator. A user interface unit operates by the control unit indicates the position of the catheter relative to the patient's diaphragm based on the selected signal. The position information may be presented in relation to signal curves representing the catheter signal or as an elongate vertical shape representing the catheter, the display unit being operated to indicate on the elongate vertical shape the position of the diaphragm.

2 Claims, 6 Drawing Sheets

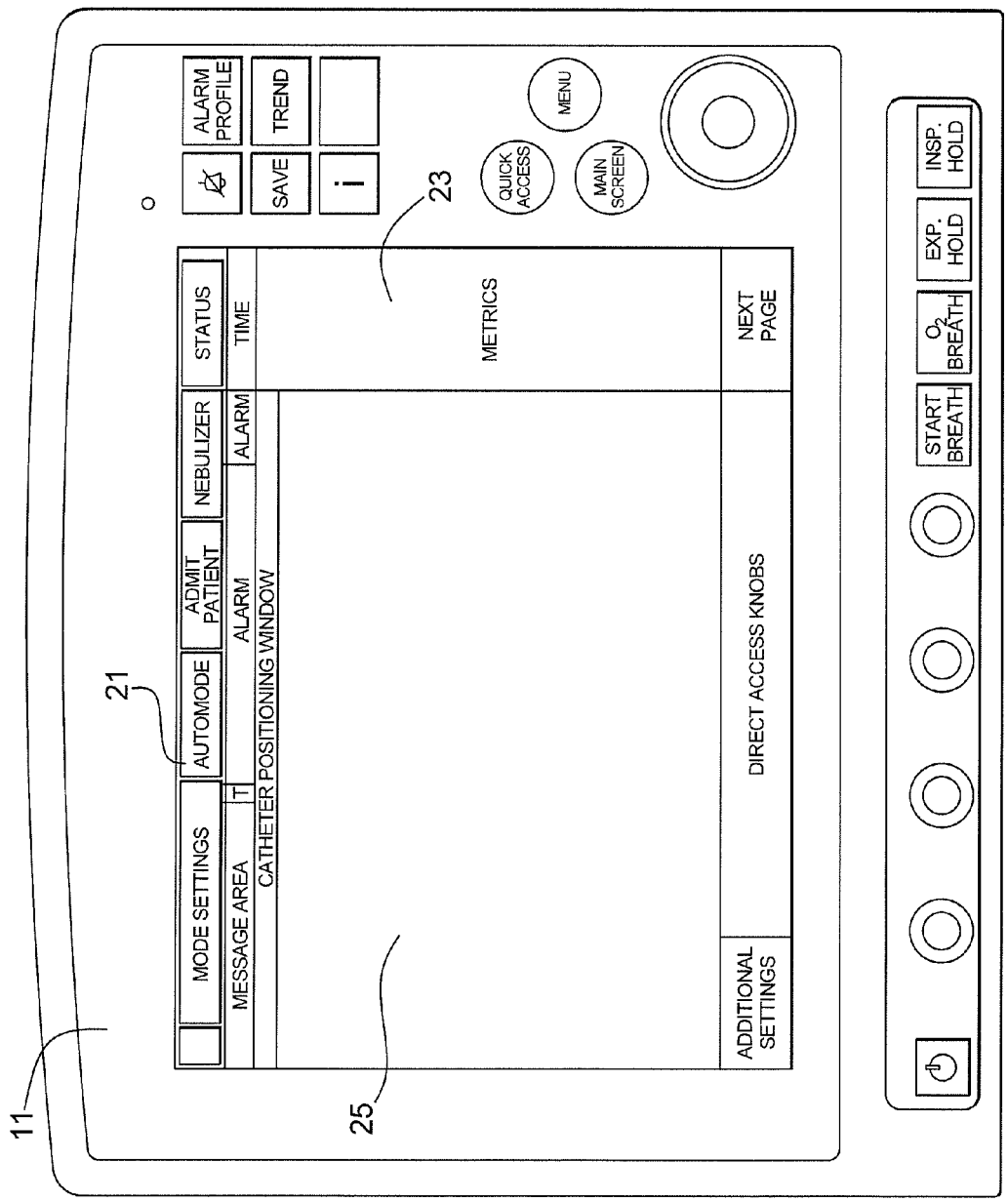

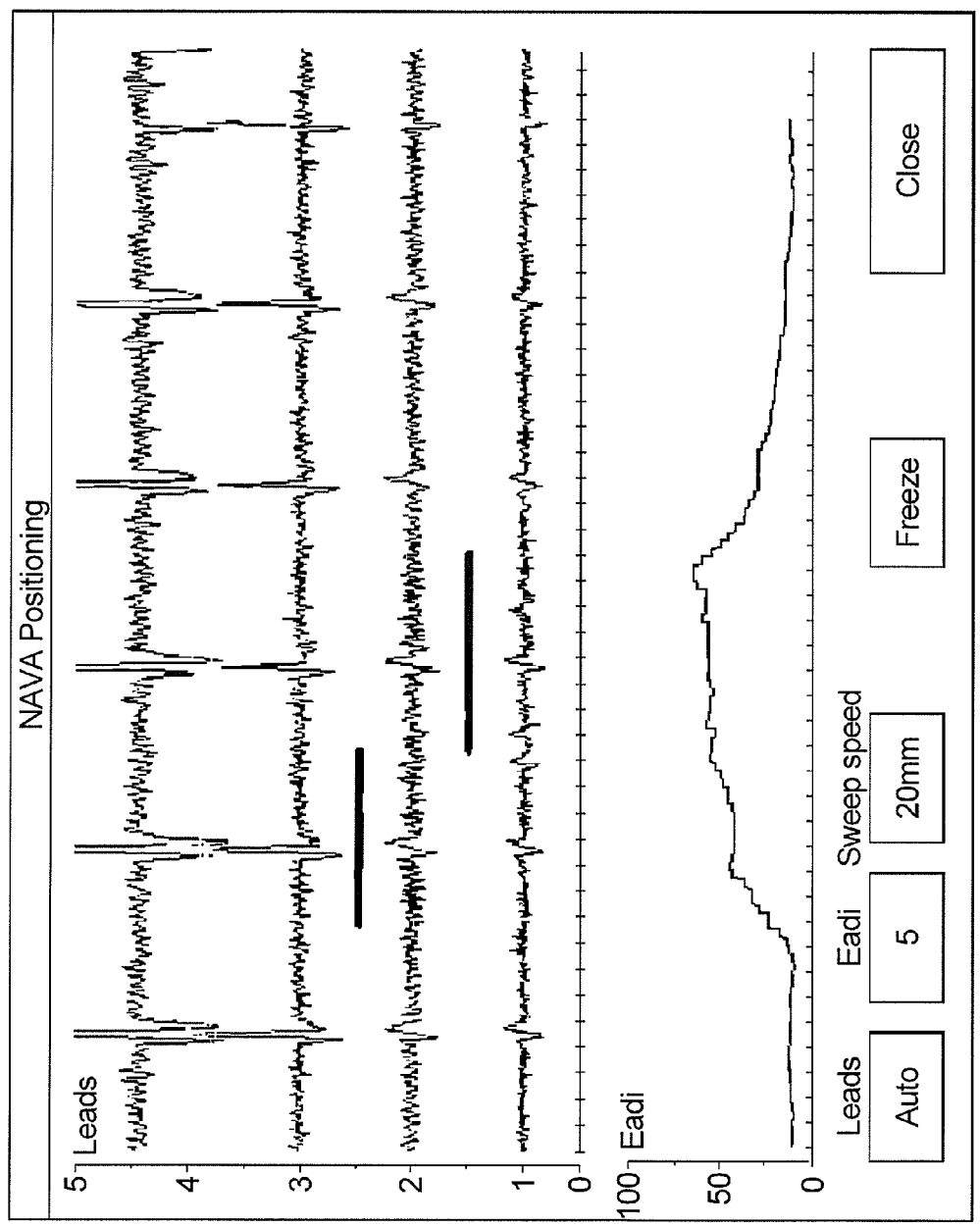

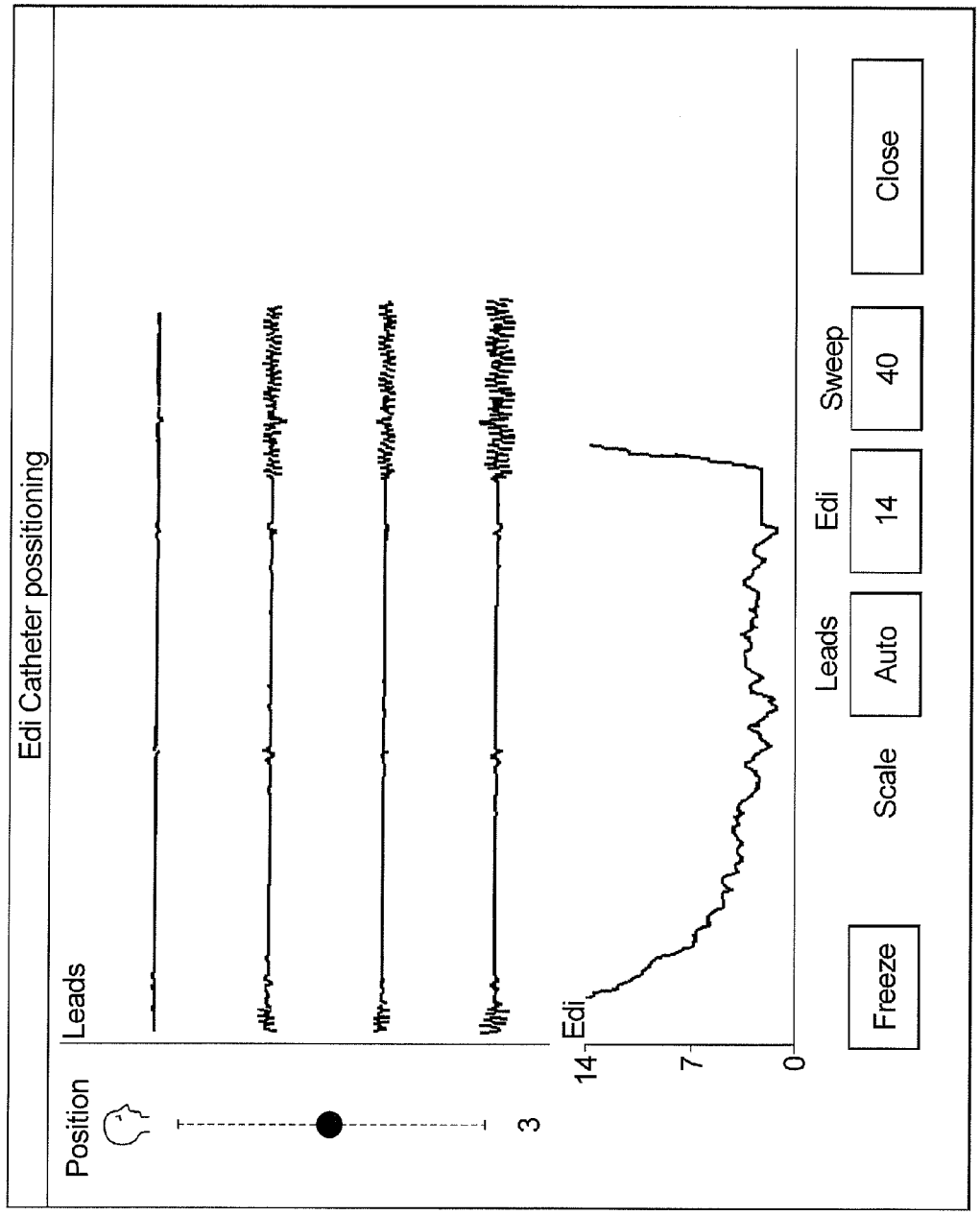

US 8,863,742 B2

CONTROL UNIT AND DISPLAY UNIT FOR AN EMG CONTROLLED VENTILATOR

BACKGROUND OF THE INVENTION

1. Field of the Invention

The present invention relates to a control unit and a display unit for an EMG controlled ventilator.

2. Description of the Prior Art

U.S. Pat. No. 5,671,752 discloses a method and a device for registering the myoelectrical activity of the diaphragm by means of an esophageal catheter having an array of electrodes. Such a signal from an esophageal catheter is prone to disturbances from other myoelectrical signals that are present in the patient's body. For improving the signal-to-noise ratio of such an electromyographic signal cross-correlation of the signals from the different electrodes in the catheter is used. Electrode pairs on opposite sides of the diaphragm but having approximately the same distance to the diaphragm will produce signals that are opposite but substantially equal in magnitude and phase. By subtracting the signals from one electrode pair from the other the two desired signals will be added, while the noise components of the two signals will substantially cancel each other out.

When a patient is breathing spontaneously but still needs breathing support the myoelectric signal from the diaphragm can be used to control the ventilator. U.S. Pat. Nos. 5,820,560 and 6,588,423 both disclose methods and devices for triggering ventilatory support to a patient using a myoelectrical signal obtained from the diaphragm. WO05/048838 discloses how to obtain an EMG signal from an esophageal catheter, taking into account the ECG signal, and in particular handling the fact that the position of the esophageal catheter relative to the diaphragm may change rapidly.

A problem when obtaining a myoelectrical signal from the diaphragm is positioning of the catheter within the patient's esophagus. To obtain a proper signal some of the electrodes should be placed above the diaphragm and some below it. There is a possibility that the catheter will be inserted too far, or not be inserted far enough. In both cases the catheter will detect a weak signal or may not capture any signal at all. The catheter may also capture myoelectrical signals from other muscles instead of, or in addition to, the signal from the diaphragm. Hence, it is difficult to obtain an optimal catheter position and the ventilator may have to work in pneumatic triggering mode if the signal is too weak.

Ensuring the correct positioning of the catheter within the patient is therefore important.

Also, the diaphragm will move up and down as the patient breathes, so that the position of the electrodes relative to the diaphragm will change to a degree that is dependent on the breathing activity of the patient. Hence, even if the esophageal catheter is placed correctly initially, it may move in such a way that it no longer records the EMG signal of the diaphragm.

There is also a risk that the catheter will be moved inadvertently, to be inserted too far into the patient or be pulled out from the patient's esophagus. Therefore, the position of the catheter should be monitored continuously to ensure that a correct signal is obtained and the operator should be notified of any changes.

SUMMARY OF THE INVENTION

An object of the invention is to monitor the positioning of an esophageal catheter used to record a myoelectric signal from the diaphragm of a patient.

The above object is achieved in accordance with the present invention by a control unit for a ventilator that provides EMG controlled ventilation to a patient, the control unit operating a user interface, and the control unit having an input that receives respective EMG signals from a number of electrode pairs of an esophageal catheter inserted into the patient, the control unit being configured to select at least one signal, from among the received signals at the input, that is to be used for controlling the ventilator, and the control unit operating the user interface to display at least some of the signal curves of the received signals in a designated field of a display of the user interface, and the control unit operates the display to indicate the position of the catheter thereon relative to the patient's diaphragm, based on the selected signal.

The object is also achieved by a user interface unit for use with a control unit according to the above, the user interface unit having a first field for displaying a number of curves representing signals from a number of electrode pairs of an esophageal catheter and indicating the position of the catheter relative to the patient's diaphragm based on at least one signal selected by the control unit to control the ventilator.

EMG controlled mode should be understood to mean a support mode in which the ventilation support is based on the EMG signal from the diaphragm.

This provides an improved user interface for the operator of an EMG controlled ventilator, which will enable faster and more reliable determination of the correct position of the esophageal catheter within the patient.

In a preferred embodiment the control unit controls the user interface unit to indicate the position of the catheter in the first field of the user interface unit in relation to the signal curves. In this case the position may be indicated by altering the presentation of the signal curve or curves, for example, the color or thickness of the curve or curves, corresponding to the at least one selected signal. Alternatively, the position may be shown on the display by an indicator between the signal curves corresponding to the at least one selected signal.

Alternatively, the control unit may control the user interface unit to indicate the position of the catheter by displaying an elongate vertical shape representing the catheter and indicating on the elongate vertical shape the position of the diaphragm.

Hence, the invention constitutes an improved user interface for use in EMG controlled ventilation.

BRIEF DESCRIPTION OF THE DRAWINGS

FIG. 2 is an overall view of a monitoring screen for monitoring a ventilator that is controlled by a myoelectrical signal.

FIGS. 3a and 3b illustrates a first man-machine interface for presenting the position of the catheter according to a first embodiment.

FIG. 4 illustrate a man-machine interface for presenting the position of the catheter according to a second embodiment.

DESCRIPTION OF THE PREFERRED EMBODIMENTS

Figure 1:
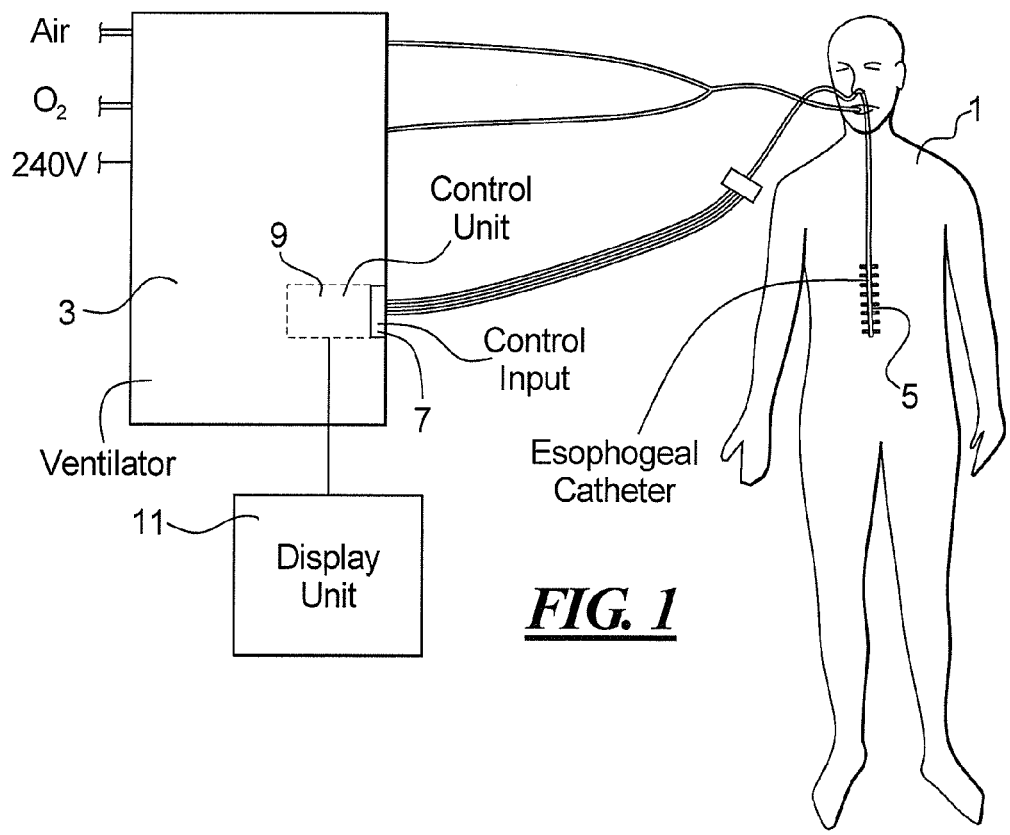
FIG. 1 illustrates a patient with an esophageal catheter used to control a ventilator.

FIG. 1 is a schematic overview of a patient 1 connected to a ventilator 3 and having an esophageal catheter 5 inserted in order to record a myoelectric signal from the diaphragm. This myoelectric signal is fed to a control input 7 of the ventilator 3 to control the ventilating function of the patient 1. The catheter 5 carries a number of electrodes, for example, nine electrodes placed equidistantly in an array along the catheter to produce 8 subsignals, each subsignal being a difference signal between two neighbouring electrodes, that is, the signal from an electrode pair. The subsignals will be processed in a control unit 9 in the ventilator to produce the overall signal that can be used to control the ventilator. To this end the control unit 9 selects the signal or signals from the electrode pairs that best represent the EMG signal. How to do this is disclosed in detail in U.S. Pat. No. 5,671,752 and WO2005/048838. The control unit 9 also controls a display unit 11 having at least a display screen for displaying information to an operator of the ventilator 3.

Typically, the signal used to control the ventilator will be taken from the electrode pairs that are in level with the diaphragm, since they contain the highest EMG signal. If the catheter is moved within the patient's esophagus the position of the electrodes relative to the diaphragm will change. In this case, other electrode pairs may contain the best EMG signal, in which case the control signal will be taken from these other electrode pairs. It is of interest to the operator to know from which electrode pair the control signal is taken, since this reflects the position of the catheter relative to the diaphragm. This position may be used as an indicator of whether or not the catheter is in an appropriate position within the patient's esophagus. For example, if the control signal is taken from the first electrode pairs, this is an indication that the catheter is not inserted far enough into the esophagus. If, on the other hand, the control signal is taken from the last electrode pairs, this indicates that the catheter should be moved to a slightly higher position within the patient.

This may be presented to the operator in several different ways, some of which will be discussed in detail below.

FIG. 2 illustrates a monitoring screen for monitoring the function of a ventilator according to an embodiment of the present invention. The screen includes a menu bar 21 and an information field 23 that are not important in the context of the invention and will not be discussed in any detail. The menu bar enables control of the ventilator and of the different views that can be presented on the screen. The information field shows ventilator parameters related to, for example, ventilator pressure and volume information, and respiratory rate.

The main field 25 may be used to display different types of information. During ongoing ventilation, whether EMG controlled or not, pressure and flow curves are displayed. The main field of the screen for catheter positioning according to a first embodiment of the invention is shown in FIG. 3.

In FIG. 3, the main field 25 has two main parts: A lower part of the main field shows the Eadi signal as a function of time, that is, the signal that is indicative of the electrical activity of the diaphragm, and that is used to control the breathing support provided by the ventilator. In FIG. 3*a* the Eadi over one breath is shown. The part of the signal between positive flank and the negative flank corresponds to the inspiration phase and the rest corresponds to the expiration phase. An upper part of the main field shows the signals received from at least some of the electrode pairs. The number of signals displayed depends on the size and resolution of the screen, and on what is considered a manageable amount of information for an operator.

In FIG. 3*a*, four electrode pair signals are shown along a time axis. The uppermost signal is taken from the uppermost electrode pairs, the lowermost signal is taken from the lowermost electrode pairs and the two intermediate signals are taken from intermediate electrode pairs of the catheter. At any given time the Eadi signal will be taken from the electrode pairs determined to give the best signal. According to a preferred embodiment the electrode pair used at any given time along the time axis to generate the control signal for the ventilator is indicated in the upper part of the main field along the relevant signal curves. In FIG. 3*a* the indication is made in the form of a horizontal line in a position corresponding to the relevant electrode pairs used. As can be seen, in a position in time corresponding to the beginning of the inspiration the signal is taken from electrode pairs in the middle of the catheter. At the end of the inspiratory phase and until the expiration starts the signal is taken from electrode pairs in the lower part of the catheter.

Figure 3B:
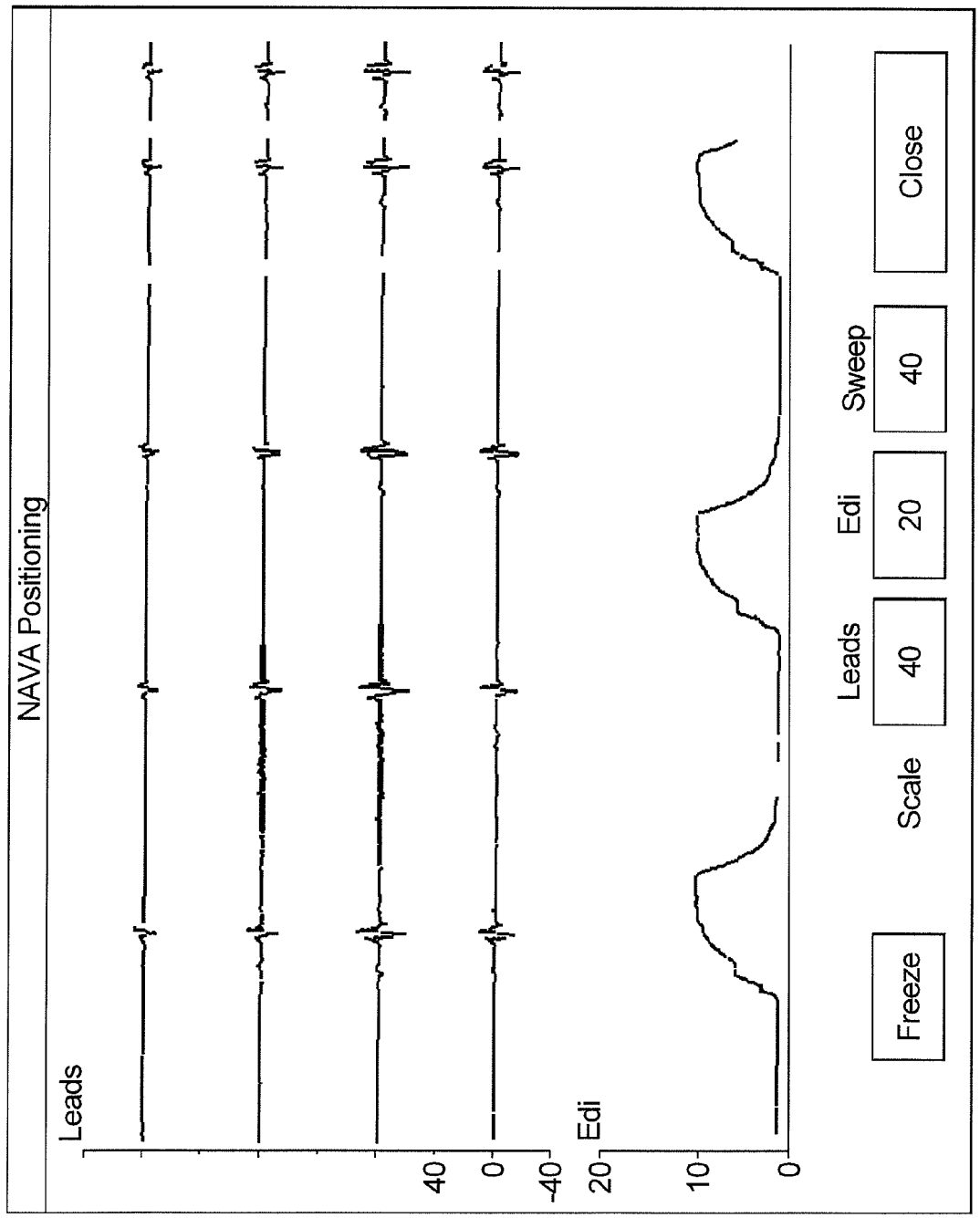

This information may also be included in the curves themselves, in several different ways. The part of a particular curve in which this curve forms the basis of the control signal may be colored in a color that distinguishes it from the rest of the curves. This color should preferably be a color that is not associated with any particular signalling function. Therefore, for example, red and green should be avoided, since they may be taken to signal that a situation is ok or not ok. Also, the color should be clearly distinguishable but not stand out so much that it takes away attention from other important information. A blue color called "cornflower blue" has been found to be suitable, but this is of course only an example. Instead of using a different color, the relevant part of the curve may be drawn in bold, or as a dashed or dotted line. The way of identifying the curve is not important as long as it is clearly distinguishable on the screen. In FIG. 3*b* the relevant part of each curve is shown in bold.

FIG. 4 shows an alternative embodiment in which, to the left of the main screen, a vertical field is shown, comprising vertical line represents the catheter. A schematically drawn head at the top of the vertical line represents the patient's head and indicates direction. A dot is placed on the vertical line in a position representing the position of the electrode pair from which the control signal is presently retrieved. A number below the vertical line indicates the number of the electrode pair. In the example shown in FIG. 4 electrode pair number 3 is currently used. This is located approximately in the middle of the catheter and therefore the dot is placed at the centre of the vertical line.

Figures 5A, 5B, 5C, 5D:
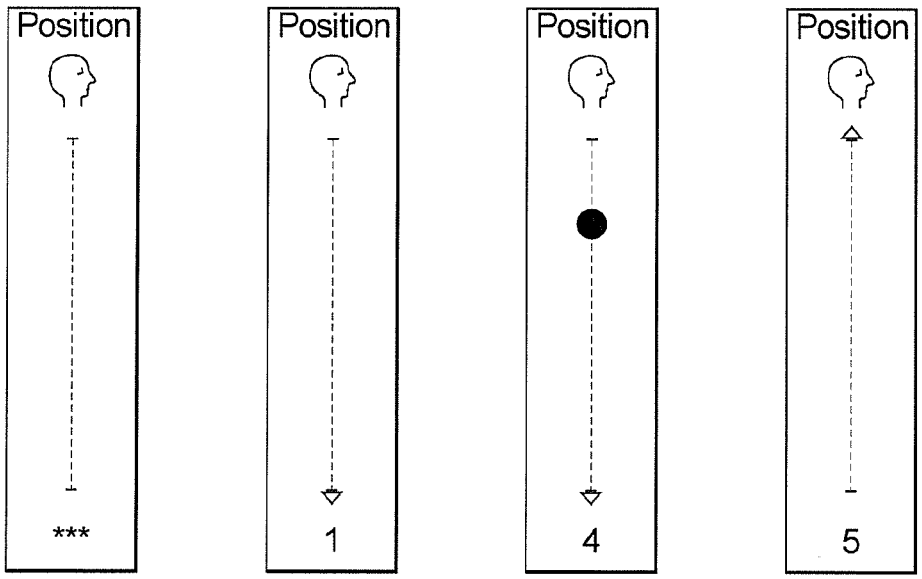
FIGS. 5a-5d illustrate a first man-machine interface for presenting the position of the catheter according to the second embodiment.

FIGS. 5*a*-5*d* illustrate the same method of indication as the vertical field in FIG. 4, that is, a vertical line representing the catheter. This indication can also be used by itself, that is, without the curves shown in the main field. In FIG. 5*a*, no dot is shown along the vertical line. Instead, three asterisks are shown below the line, to indicate that no position of the catheter can be determined. In FIG. 5*b* electrode pair number 1 is indicated. Again, there is no dot. Instead there is an arrow pointing downwards at the bottom of the vertical line, to indicate that the catheter should be inserted deeper into the esophagus to maintain the signal. In FIG. 5*c* the signal is taken from electrode pair number 4. A dot marks the part of the vertical line corresponding to the position of electrode pair number 4 on the catheter. Since this electrode pair is not too close to either end of the catheter, no arrow is used to indicate a desired movement. In FIG. 5*d* the signal is taken from electrode pair number 5. This is the uppermost electrode pair and therefore an arrow is presented at the top of the vertical line to indicate that the catheter should be pulled upwards.

Figure 6F:
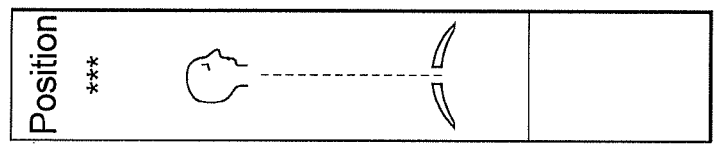
FIGS. 6a-6f illustrate a first man-machine interface for presenting the position of the catheter according to a third embodiment which is currently the preferred embodiment.
Figure 6E:
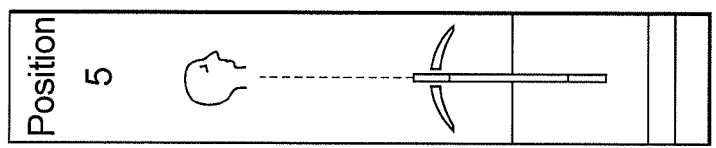
Figure 6D:
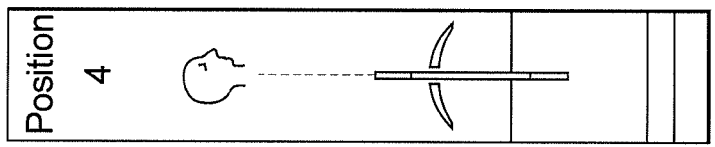
Figure 6C:
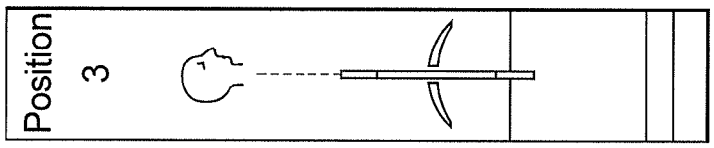
Figure 6B:
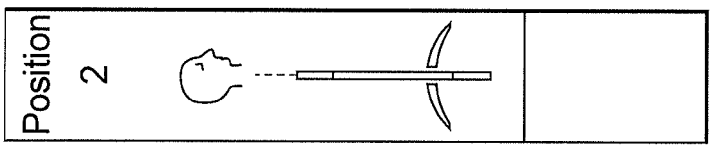
Figure 6A:
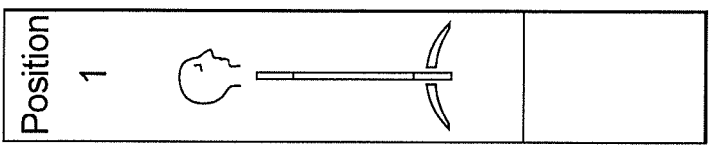

FIGS. 6*a*-6*f* illustrate an alternative method to that of FIGS. 5*a*-5*d* of presenting the position of the catheter in the patient's esophagus. This may be used alone, or instead of the vertical line in the vertical field of FIG. 4. A slightly wider vertical line represents the catheter. The ends of the vertical line are preferably marked in a different color than the rest. The position of the diaphragm is shown as a curved horizontal line across the vertical line. In this way, the operator can easily see when the diaphragm is too close to one end of the catheter so that the catheter position should be adjusted. A number above the head indicates the number of the electrode pair from which the control signal is retrieved. In FIG. 6a the signal is taken from electrode pair number 1, which means that the lower end of the catheter is located near the diaphragm. This can also be seen by the position of the vertical line relative to the diaphragm. The line indicating the diaphragm is here drawn across the end of the vertical line which has a different color to the main part of the line. In FIG. 6b the signal is taken from electrode pair number 2, in FIG. 6c from electrode pair number 3 and in FIG. 6c from electrode pair number 4. The position of the vertical line relative to the horizontal line in each case indicates the position of the catheter relative to the diaphragm. In FIG. 6d the signal is taken from electrode pair number 5, which is the uppermost electrode pair, and the vertical line representing the catheter is so low in relation to the horizontal line as to indicate that the diaphragm is now at the upper end of the catheter. In FIG. 6f there is no signal from the catheter, which is indicated by three asterisks above the head. This indicates that the catheter may be in the wrong position, although there may be other reasons. For example, if the patient is sedated the signal may be too weak. Hence, the position of the catheter should be checked to se if it should be changed in order to pick up an appropriate EMG signal.

If appropriate a message may be displayed to the operator in a suitable field of the screen, for example "check catheter position" or in which direction the catheter should be moved to reach a better position. This may be in addition to the information discussed above, or as an alternative.

As mentioned above, the type of information displayed in the main field 25 of the screen may vary with time depending on the situation. Typically during ventilation pressure and/or flow curves may be displayed. The vertical indicators, according to the invention, as shown in FIGS. 5a-5d and FIGS. 6a-6f, may of course be displayed independently of the type of information displayed in the main field. Hence, these vertical embodiments make it possible to indicate the catheter position even if other information is being displayed in the main field.

Although modifications and changes may be suggested by those skilled in the art, it is the intention of the inventors to embody within the patent warranted heron all changes and modifications as reasonably and properly come within the scope of their contribution to the art.

The invention claimed is:

1. A control and display system for operating a ventilator that provides EMG controlled ventilation to a patient using an esophageal catheter inserted into the patient that carries a plurality of electrodes at respective positions along a length of the catheter and thereby causing said electrodes to be located at respectively different distances from the diaphragm of the patient, said control and display system comprising:

a control unit having an input that receives a plurality of signals, each exhibiting a signal curve, respectively obtained from a plurality of electrode pairs among said electrodes carried by said esophageal catheter;

said control unit being configured to automatically analyze said plurality of signals in order to also automatically select at least one signal, as a selected signal, from among said plurality of signals, that has a highest likelihood of originating from an electrode pair closest to the diaphragm and thus best represents an EMG signal for use in controlling said ventilator;

a display connected to said control unit, at which said control unit is configured to display at least some of the respective signal curves of said plurality of signals, including the signal curve of said selected signal, with an initial color and an initial thickness that are the same for all of said signal curves prior to inserting the catheter;

said control unit being configured to also display, at said display, a graphically displayed line having a length that represents said length of said catheter, with the respective signal curves displayed next to and along said length of said line at respective positions corresponding to an electrode pair from which the respective signal curve was obtained; and said control unit being configured to operate said display by altering at least one of initial color and initial thickness said of the signal curve corresponding to said at least one selected signal, to give said signal curve corresponding to said selected signal a color or thickness that differs from said initial color or initial thickness, while maintaining the other signal curves with said initial color and initial thickness at said display, the position at said display of the signal curve with an altered color or thickness next to said graphically displayed line forming a visual indicator of whether said catheter is correctly positioned in the patient and thereby also forming a visual indication of a need to reposition said catheter.

2. A breathing assist system comprising:

a ventilator comprising a breathing circuit adapted to interact with a patient;

an esophageal catheter adapted for insertion into the patient, said esophageal catheter carrying a plurality of electrodes, at respective positions along a length of the catheter and thereby causing said electrodes to be located at respectively different distances from the diaphragm of the patient, that each electrode being adapted to detect and emit an emitted signal;

a control unit that controls operation of said breathing circuit of said ventilator to provide breathing assistance to the patient, said control unit having an input that receives the emitted signals respectively from a plurality of pairs of said electrodes, said control unit being configured to automatically analyze said plurality of signals in order to also automatically select at least one signal, as a selected signal, from among said plurality of emitted signals that has a highest likelihood of originating from an electrode pair closest to the diaphragm and thus best represents an EMG signal for use in controlling said breathing circuit;

a display connected to said control unit, at which said control unit is configured to display at least some of the respective signal curves of said plurality of signals, including the signal curve of said at least one selected signal, with an initial color and an initial thickness that are the same for all of said signal curves prior to inserting the catheter;

said control unit being configured to also display, at said display, a graphically displayed line having a length that represents said length of said catheter, with the respective signal curves displayed next to and along said length of said line at respective positions corresponding to an electrode pair from which the respective signal curve was obtained; and said control unit being configured to operate said display by altering at least one of said initial color and initial thickness of the signal curve corresponding to said at least one selected signal, to give said signal curve corresponding to said selected signal a color or thickness that differs from said initial color or initial thickness, while maintaining the other signal curves with said initial color and initial thickness at said display, the position at said display of the signal curve with an altered color or thickness next to graphically displayed line forming a visual indicator of whether said catheter is correctly positioned in the patient and thereby also forming a visual indication of a need to reposition said catheter.

\* \* \* \* \*